United States Patent
Lendlein et al.

(10) Patent No.: US 11,618,980 B2
(45) Date of Patent: Apr. 4, 2023

(54) SURFACE-FUNCTIONALISED POLYMERIC OBJECT AND METHOD OF ITS PRODUCTION

(71) Applicant: Helmholtz-Zentrum Geesthacht Zentrum Fuer Material-Und Kuestenforschung GmbH, Geesthacht (DE)

(72) Inventors: Andreas Lendlein, Berlin (DE); Axel Thomas Neffe, Berlin (DE); Paul Jakob Hommes-Schattmann, Berlin (DE); Quanchao Zhang, Jiangxi (CN)

(73) Assignee: HELMHOLTZ-ZENTRUM HEREON GMBH, Geesthacht (DE)

( * ) Notice: Subject to any disclaimer, the term of this patent is extended or adjusted under 35 U.S.C. 154(b) by 458 days.

(21) Appl. No.: 16/623,256

(22) PCT Filed: Sep. 26, 2018

(86) PCT No.: PCT/EP2018/076146
§ 371 (c)(1),
(2) Date: Dec. 16, 2019

(87) PCT Pub. No.: WO2019/063627
PCT Pub. Date: Apr. 4, 2019

(65) Prior Publication Data
US 2020/0172688 A1 Jun. 4, 2020

(30) Foreign Application Priority Data

Sep. 28, 2017 (EP) .................................... 17193860

(51) Int. Cl.
*D01F 8/14* (2006.01)
*C08J 7/04* (2020.01)
*D01D 5/00* (2006.01)

(52) U.S. Cl.
CPC .............. *D01F 8/14* (2013.01); *C08J 7/0427* (2020.01); *D01D 5/003* (2013.01); *D01D 5/0053* (2013.01);
(Continued)

(58) Field of Classification Search
None
See application file for complete search history.

(56) References Cited

U.S. PATENT DOCUMENTS

| 5,484,881 A * | 1/1996 | Gruber | A61L 31/06 |
| | | | 156/244.11 |
| 2005/0161857 A1* | 7/2005 | Coombes | D01F 6/625 |
| | | | 264/331.12 |

(Continued)

FOREIGN PATENT DOCUMENTS

| CN | 102245125 A | 11/2011 |
| CN | 106492274 A | 3/2017 |

(Continued)

OTHER PUBLICATIONS

European Search Report dated Apr. 10, 2018 in EP 17193860.8.
(Continued)

*Primary Examiner* — Jeffrey D Washville
(74) *Attorney, Agent, or Firm* — Fox Rothschild LLP (57) ABSTRACT

The invention provides a surface-functionalised polymeric object (10), comprising: a bulk material (11) comprising a copolymer containing constitution units derived from a first comonomer and constitution units derived from a second comonomer, the first comonomer being selected from L-lactide and D-lactide and forming sequences of oligo(L-lactide) or oligo(D-lactide) in the copolymer the copolymer having a substantially random, partially blocky structure with a dyad ratio of (lactide-lactide)-dyads to (lactide-second comonomer)-dyads of at least 2.0:1; and a surface layer (12)

(Continued)

disposed on a surface of the bulk material (11), the surface layer (12) comprising a functionalising species and at least one chain of poly(D-lactide) or of poly(L-lactide) covalently bound to the functionalising species, and at least one chain being different from the oligo(L-lactide) sequences or oligo (D-lactide) sequences contained in the copolymer; wherein the surface layer (12) is attached to the bulk material (11) via stereocomplexes formed between the poly(D-lactide) chain(s) of the functionalising species and the oligo(L-lactide) sequences contained in the copolymer or via stereocomplexes formed between the poly(L-lactide) chain(s) of the functionalising species and the oligo(D-lactide) sequences contained in the copolymer, respectively. The surface-functionalised polymeric object can be produced in a one-step procedure by coaxial electrospinning.

14 Claims, 6 Drawing Sheets (52) U.S. Cl.
CPC ........ *C08J 2367/04* (2013.01); *C08J 2467/04* (2013.01)

(56) References Cited

U.S. PATENT DOCUMENTS

2010/0312340 A1* 12/2010 Hissink ................. C08G 63/08
528/357
2015/0057385 A1 2/2015 Hong et al.

FOREIGN PATENT DOCUMENTS

EP         1334990 A1    8/2003
JP      2016210894 A    12/2016

OTHER PUBLICATIONS

Sachiro Kakinoki et al: "Surface Modification of Poly(L-lactic acid) Nanofiber with Oligo(D-lactic acid) Bioactive-Peptide Conjugates for Peripheral Nerve Regeneration",Polymers, vol. 3, No. 2, Apr. 27, 2011 (Apr. 27, 2011),pp. 820-832.
International Search Report dated Oct. 25, 2018 in PCT/EP2018/076146.
Li et al., "Recent advances in stereocomplexation of enantiomeric PLA-based copolymers and applications", Progress in Polymer Science, 62, 2016, 22-72.

* cited by examiner

SURFACE-FUNCTIONALISED POLYMERIC OBJECT AND METHOD OF ITS PRODUCTION

CROSS-REFERENCE TO RELATED APPLICATIONS

This application is a § 371 national phase entry of International Patent Application No. PCT/EP2018/076146, filed on Sep. 26, 2018, which claims priority to and the benefit of European Patent Application No. 17193860.8, filed on Sep. 28, 2017, both of which are hereby incorporated herein by reference in their entireties.

The work leading to this invention has received funding from the European Union Seventh Framework Programme FP7/2007-2013 under Grant Agreement n° 604049.

The invention is directed to a surface-functionalised polymeric object comprising a polymeric bulk material and a functionalising surface layer. The invention is further related to a method of producing a porous, surface-functionalised object by electrospinning.

Usually polymers are selected by their physical or chemical bulk properties according to the target application or their processability. However, often specific surface characteristics are required in the respective application that the polymer does not have. For instance haemocompability may be required in medical applications. Here, surface functionalisations are applied which impart the desired surface characteristic to the bulk material. The functionalisation has to be stable at the conditions of use.

The bulk material may be subjected to the surface modification in a post-processing step after processing the bulk material into a device. Post-processing approaches allow for a wide variety of functionalisations but involve additional process steps. On the other hand, other approaches integrate the surface functionalisation in the production process, thereby reducing the number of processing steps but potentially limiting its flexibility.

Many surface functionalisations are based on covalent binding of the functionalising compound to the surface. Covalent functionalisations usually must be effected by post-processing methods involving additional process steps. Moreover, the chemical reaction required for the covalent binding may induce an undesirable change of the surface or of the bulk characteristics of the material. In case of medical applications involving a biodegradation of the material, covalent modifications lead to high investments for the necessary medical approval of the material.

Non-covalent functionalisations by way of pure physisorption, e.g. via hydrophobic/hydrophobic interactions, are also known. However, on long-term the physisorbed species will inevitably be separated from the surface. In case of hydrophilic or water soluble compounds such as RGD-peptides or proteins used for cell adhesion to the surface, rather fast release in minutes or hours is observed at physiological conditions.

The formation of stereocomplexes between poly(D-lactide) (PDLA) and poly(L-lactide) (PLLA) at surfaces or boundary surfaces has been used for adjusting the roughness or hydrophilic properties of a surface (Recent advances in stereocomplexation of enantiomeric PLA-based copolymers and applications, Zibiao Li, Beng Hoon Tan, Tingting Lin, Chaobin He, Progress in Polymer Science, 2016, Vol. 62, p. 22-72). In one case, a biological functionalisation of surfaces based on this kind of supramolecular interaction was reported (Polymers 2011, Vol. 3, 820-832). Here, the interior of an electrospun porous tube of PLLA was functionalised with a peptide via an oligo(D-lactide)-linker coupled to the peptide's N-terminus and forming stereocomplexes with the PLLA. Further, the suitability of the functionalised tube as artificial nerve channel was investigated.

However, for the following reasons the afore-mentioned approach has limited suitability for medical applications. The glass transition $T_g$ of PLLA is between 50 and 60° C. Hence, at physiological temperatures PLLA has low elasticity, and as bulk material, it has a very high elastic modulus (E-modulus) in the GPa range. Thus, PLLA is not suitable when in medical applications at physiological conditions high elasticity, low E modulus and high form stability are indispensable. Moreover, the afore-mentioned method of electrospinning using a mixed solution of a polymer (e.g. PLLA) and the functionalising species (e.g. peptide) may lead to a more or less homogenous distribution of the functionalising species over the complete cross-section of the polymeric nano- or microfibers. Particularly at low mixing ratios, only a very low fraction of the functional species is located on the surface of the polymeric fibers and thus available for interactions with the environment. At high mixing ratios of the functional species, however, a strong alteration of the physical properties of the polymeric fibers occurs.

BRIEF DESCRIPTION OF THE INVENTION

Accordingly, there is a demand for surface-functionalised polymeric objects, such as fibers or films, being suitable to be used in medical applications which overcome the afore-mentioned problems. The functionalisation of the object should be stable at physiological conditions. Ideally the object should have high elasticity with low elastic modulus at the temperature of use. There is also a demand of providing a feasible process of producing such surface-functionalised polymeric objects.

These objects are at least partially solved by a surface-functionalised polymeric object and a method of its production as defined in the independent claims. Further embodiments of the invention are subject of the dependent claims.

The surface-functionalised polymeric object according to the present invention comprises or consists of:
  a bulk material comprising a copolymer (or its blend with other polymers) containing constitution units derived from a first comonomer and constitution units derived from a second comonomer, the first comonomer being selected from L-lactide and D-lactide and forming sequences of oligo(L-lactide) or oligo(D-lactide) in the copolymer, the copolymer having a substantially random, partially blocky structure with a dyad ratio of (lactide-lactide)-dyads to (lactide-second comonomer)-dyads of at least 2.0:1, and
  a surface layer disposed on a surface of the bulk material, the surface layer comprising a functionalising species and at least one chain of poly(D-lactide) or of poly(L-lactide) covalently bound to the functionalising species, the at least one chain being poly(D-lactide) when oligo(L-lactide) segments are present in the copolymer and being poly(L-lactide) when oligo(D-lactide) segments are present in the copolymer,
  wherein the surface layer is attached to the bulk material via stereocomplexes formed between the poly(D-lactide) chain(s) of the functionalising species and the oligo(L-lactide) sequences contained in the copolymer or via stereocomplexes formed between the poly(L- lactide) chain(s) of the functionalising species and the oligo(D-lactide) sequences contained in the copolymer, respectively.

According to the invention, the bulk material comprises a lactide-based copolymer having either sequences of oligo (L-lactide) (oligo-LLA) or oligo(D-lactide) (oligo-DLA) and a second comonomer. Due to the second comonomer present in the copolymer its elastic properties can be adjusted according to the target application of the object. More specifically, if for instance the second comonomer is ε-caprolactone (CL), the comonomer allows to adjust the glass transition temperature of the copolymer such as to be well below the use temperature of the intended application, particularly well below 20° C. In this way, the copolymer may be tuned to be elastic at room temperature.

Moreover, when during production the functionalising molecule having at least one chain of poly(D-lactide) or of poly(L-lactide) covalently bound is brought in contact with the bulk material comprising the copolymer, stereocomplexes between oligo-LLA sequences of the copolymer and PDLA chains of the functionalising species or between oligo-DLA sequences of the copolymer and PLLA chains of the functionalising species will readily form. The stereocomplexes in form of pairs of oligo-LLA/PDLA or oligo-DLA/PLLA between the two stereoisomers of lactide (LA) form crystallites acting as physical (non-covalent) bonds between the bulk material and the functionalising species. The crystallites have a melting point at 180° C. or higher and are stable up to the time the material will degrade in physiological environment. Although being a non-covalent bond, the stability of the bonding resembles those of covalent bonds.

The surface-functionalised polymeric object according to the invention has the following characteristics:
  high strength and stability of the attachment of the surface functionalisation in a wide temperature range even at physiological conditions
  the surface functionalisation can be integrated in the production process and does not require an additional processing step
  elastic properties (elongation at break, elastic modulus, shape stability) may be adjusted by kind and amount of the second comonomer units in the copolymer of the bulk material
  accessible for a wide variety of the functionalising species
  biological/hydrolytic degradability
  high biocompatibility Another aspect of the invention is related to a method of producing a surface-functionalised polymeric object according to the invention. The method comprises:
  providing a first solution of the copolymer (or its blend with other polymers) derived from a first comonomer and a second comonomer, the first comonomer being selected from L-lactide and D-lactide and forming sequences of oligo(L-lactide) or oligo(D-lactide) in the copolymer;
  providing a second solution of the functionalising species having at least one chain of poly(D-lactide) or of poly(L-lactide) covalently bound to it; and
  subjecting the first and second solution to coaxial electrospinning to produce fibers having a core of the copolymer and a surface layer of the functionalising molecule.

Thus, by way of coaxial electrospinning from separate solutions the surface-functionalised object, here in form of a porous scaffold comprising of polymeric nano- or microfibers, can be produced in a single step. The stereocomplexes between the bulk material and the functionalising species will form readily upon evaporation of the solvent or after annealing the electrospun scaffold above the $T_g$ of PLA (>50° C.). As the functionalising species is bound on the outer surface of the polymeric fibers, it is highly accessible for interactions with the environment. The surface-functionalised fibers produced in this way may be deposited such as to form non-woven fibrous structures built-up by the fibers.

Further embodiments of the invention are subject of the dependent claims.

In the absence of an indication to the contrary, the various embodiments of the invention disclosed in the present claims, description or figures may be combined with each other.

DETAILED DESCRIPTION OF THE INVENTION

The invention will be described in more detail by way of examples. The Figures show.

The invention provides a surface-functionalised polymeric object. The object comprises or consist of:
  a bulk material comprising a copolymer (or its blend with other polymers) containing constitution units derived from a first comonomer and constitution units derived from a second comonomer, the first comonomer being selected from L-lactide and D-lactide and forming sequences of oligo(L-lactide) or oligo(D-lactide) in the copolymer, the copolymer having a substantially random, partially blocky structure with a dyad ratio of (lactide-lactide)-dyads to (lactide-second comonomer)-dyads of at least 2.0:1, and a surface layer disposed on the surface of the bulk material, the surface layer comprising a functionalising species and at least one chain of poly(D-lactide) or of poly(L-lactide) covalently bound to the functionalising species, the at least one chain being poly(D-lactide) when oligo(L-lactide) segments are present in the copolymer, while the one chain is from poly(L-lactide) when oligo(D-lactide) segments are present in the copolymer, wherein the surface layer is attached to the bulk material via stereocomplexes formed between the poly(D-lactide) chain(s) of the functionalising species and the oligo(L-lactide) sequences contained in the copolymer or via stereocomplexes formed between the poly(L-lactide) chain(s) of the functionalising species and the oligo(D-lactide) sequences contained in the copolymer, respectively.

The combination of constitution units derived from L-lactide and constitution units derived from D-lactide in the bulk material on the one hand and in the surface layer on the other hand allows for the formation of stereocomplexes between sequences of poly(L-lactide) (PLLA), present in the bulk material or the surface layer, and the complementary sequences of poly(D-lactide) (PDLA), present in the surface layer or in the bulk material, respectively. The stereocomplexes form stable crystallites acting as physical (non-covalent) bonds at the boundary interface.

Functionalising Species

The functionalising species is a compound that imparts a desired property to the surface of the bulk material. Depending of an intended use of the object typical desired surface properties comprise hydrophilic properties, hydrophobic properties, oleophobic properties, haemocompatible properties, (non)cytotoxic properties, and others. The species is selected by these properties. In order to provide the surface with different properties, two or more functionalising species may be combined in the surface layer.

The functionalising species of the surface layer may be a macro-molecule (high-molecular weight molecule) or a low-molecular weight molecule. Typically, macro-molecules have a molecular weight of 5 kDa or more. The macro-molecule may be a polymer built by one or more repetition units. The polymer may be a synthetic polymer or a biopolymer and may have a linear, branched or hyperbranched structure. The biopolymer may be selected from proteins (such as gelatin, collagen, laminin, fibronectin, fibrinogen etc.), polysaccharides (such as (e.g. hyaluronan, chondroitin sulfate, heparin, heparan sulfate, keratin sulfate etc.), glycoproteins, proteoglycans, poly nucleotides, lignin, hydrocarbons, and others. Synthetic polymers include those having functional groups as terminal and/or side groups. Examples of synthetic polymers include polyethylene glycol or polyglycerol-based systems. Likewise, the low-molecular weight molecule may be a synthetic organic molecule or a biomolecule. Typical kinds of low-molecular weight molecules comprise drugs, short peptides (≤20 amino acids), dyes, labels and others.

The functionalising species is covalently (i.e. via a chemical bond) functionalised with at least one polylactide chain (either PLLA or PDLA). The purpose of the polylactide chain(s) of the functionalising species is to form stereocomplexes with oligolactide sequences of the copolymer contained in the bulk material. Accordingly, the polylactide chain of the functionalising species is selected from poly (D-lactide) and poly(L-lactide) such that the lactide chain includes the complementary isomer with respect to the bulk material. More specifically, when the copolymer of the bulk material contains constitution units derived from L-lactide the functionalising species is functionalised with chains of poly(D-lactide). If the copolymer of the bulk material contains constitution units derived from D-lactide the functionalising species is functionalised with chains of poly(L-lactide).

In preferred embodiments, the functionalising species has two or more chains of poly(D-lactide) or of poly(L-lactide) covalently bound to it. If the species is provided with more than one polylactide chain, the stability of the attachment of the surface layer to the bulk material is increased. Particularly in the case of macro-molecules as functionalising species, it is preferred to covalently functionalise it with multiple polylactide chains.

However, the invention also encompasses single polylactide-modifications of the functionalising species, particularly in case of small, low molecular weight molecules.

For the purpose of the present description, the term "poly(L-lactide)" or "poly(D-lactide)" comprises short chains, also referred to as oligo(L-lactide) or oligo(D-lactide), as well as long chains of the respective lactide. Thus, a poly(L-lactide) or poly(D-lactide) may be as short as containing three repetition units.

However, according to preferred embodiments the poly (L-lactide) or poly(D-lactide) chains covalently bound to the functionalising species have a weight average molecular weight $M_w$ in the range of 1 to 40 kDa, particularly in the range of 5 to 30 kDa, preferably in the range of 10 to 20 kDa, more.

The covalent modification of the functionalising species with the poly(L-lactide) or poly(D-lactide) chains may be performed by specifically reacting PLLA or PDLA bearing a defined nucleophilic end group with a defined electrophilic functional group of the functionalising species, or by specifically reacting PLLA or PDLA bearing a defined electrophilic end group with a defined nucleophilic functional group of the functionalising species, respectively. As an example, PDLA bearing a terminal thiol group is reacted with methacrylate-functionalised gelatin, forming a covalent bond between PDLA and gelatin by the specific addition of the nucleophilic thiol group to an electrophilic methacrylate group via conjugated addition (FIG. 1).

The thiol functionalised PDLA may be synthesized by ring-opening polymerisation of D,D-dilactide using bis(2-hydroxyethyl)disulfide as initiator, followed by reduction of the resulting PDLA-bisulfide with tri(n-butyl)phosphine. The functionalisation of gelatin with methacrylate groups can be performed be specifically reacting primary amine groups present in gelatin with glycidyl methacrylate.

Bulk Material

The bulk material comprises or consists of a copolymer containing constitution units derived from a first comonomer and constitution units derived from a second comonomer. The first comonomer being selected from L-lactide (LLA) and D-lactide (DLA) and forms sequences of oligo(L-lactide) (oligo-LLA) or oligo(D-lactide) (oligo-DLA) in the copolymer. The copolymer may be a dicopolymer exclusively being based on the first and the second comonomer. Alternatively, the copolymer may contain one or more further comonomers.

The copolymer has a substantially random, partially blocky structure. Random copolymers include a statistically arbitrary distribution of the repetition units and are obtained by copolymerising the comonomers from a mixed solution or melt. The term "partially blocky" means that the copolymer comprises some block sequences of oligo(L-lactide) or oligo(D-lactide), respectively. Thus, a sequence of oligo (L-lactide) or oligo(D-lactide) in the copolymer may be as short as containing three repetition units of the corresponding lactide. The block sequences of oligo(L-lactide) or oligo(D-lactide) in the copolymer allow the formation of stereocomplexes with the corresponding complementary chains, i.e. poly(D-lactide) or poly(L-lactide), attached to the functionalising species.

The degree of block segment length in copolymers can be expressed by the average dyad ratio. The dyad ratio is the molar ratio of the number of homodimers of the same type of comonomer present in the copolymer chain (comonomer 1-comonomer 1) to a heterodimer formed by two different comonomers (comonomer 1-comonomer 2). The dyad ratio can be determined by $^1$H-NMR (nuclear magnetic resonance) spectroscopy. According to the present invention, the copolymer has a dyad ratio of (lactide-lactide)-dyads to (lactide-second comonomer)-dyads of at least 2.0:1, particularly of at least 2.5:1. When the dyad ratio is less than 2.0:1 the occurrence of blocks of oligolactide in the copolymer becomes low so that the formation of stereocomplexes with the polylactide chain(s) of the functionalising species also becomes low. The preferred dyad ratio may change with the selection of the second comonomer. According to an embodiment of the invention, the second comonomer of the copolymer is ε-caprolactone and preferably the dyad ratio of lactide-lactide dyads (LA-LA) to lactide-ε-caprolactone dyads (LA-CL) of at least 2.5:1.

In embodiments, a weight content of L-lactide or D-lactide in the copolymer of the bulk material is in the range 55 to 90 wt %, particularly in the range of 56 to 67 wt %, preferably in the range of 60 to 64 wt % based on the total weight of the copolymer. When the weight content of L- or D-lactide in the copolymer is less than 55 wt %, the formation of the olgiolactide blocks during the synthesis may be hindered resulting in low formation of stereocomplexes with the polylactide chains of the surface layer and poor binding strength. If however the weight content L- or D-lactide in the copolymer is more than 90 wt %, the glass temperature $T_g$ of the copolymer will increase with the effect that the material at room temperature is in the glassy state, i.e. that the material is not elastic.

In preferred embodiments, the second comonomer of the copolymer is ε-caprolactone, that is the copolymer of the bulk material is selected from poly[(L-lactide)-co-(ε-caprolactone)] and poly[(D-lactide)-co-(ε-caprolactone)].

The weight content of ε-caprolactone in poly[(L-lactide)-co-(ε-caprolactone)] or poly[(D-lactide)-co-(ε-caprolactone)] may be in the range of 25 to 47 wt %, particularly in the range of 33 to 44 wt %, preferably in the range of 36 to 40 wt %, based on the total weight of the copolymer (100 wt %). When the weight content of ε-caprolactone in the copolymer is less than 25 wt %, the glass temperature $T_g$ of the copolymer will increase with the effect that the material at room temperature is in the glassy state, i.e. that the material is not elastic. If however the weight content of ε-caprolactone in the copolymer is more than 47 wt %, the formation of the oligolactide blocks during the synthesis may be hindered resulting in low or no formation of stereocomplexes between the bulk copolymer and the polylactide chains of the functionalising species on the surface.

The function of ε-caprolactone in the copolymer is to form an amorphous phase with a $T_g$ well below the desired temperature of use, particularly room temperature. For this purpose a fraction of ε-caprolactone present in an amorphous phase of the copolymer is at least 25 mol %, preferably in the range of 27-33 mol %, based on the total molar amount of ε-caprolactone in the copolymer.

The copolymer poly[(L-lactide)-co-(ε-caprolactone)] or poly[(D-lactide)-co-(ε-caprolactone)] can be synthesised by copolymerising a mixture of the comonomers ε-caprolactone and L,L-dilactide or ε-caprolactone and D,D-dilactide in the desired mixing ratio through ring opening copolymerisation.

In embodiments, the copolymer, particularly when selected from poly[(L-lactide)-co-(ε-caprolactone)] and poly[(D-lactide)-co-(ε-caprolactone)], has a weight average molecular weight ($M_w$) of at least 80 kDa, preferably of at least 100 kDa. A high molecular weight of ≥80 kDa enhances the elasticity of the material by increasing the entanglement of the polymer chains. The upper value of the molecular weight of the first polymer component is not particularly limited in terms of material properties. However, it may be difficult to achieve molecular weights $M_w$ of more than 300 kDa by standard synthesis methods of the copolymer. The weight average molecular weight $M_w$ can be measured by universally calibrated gel permeation chromatography (GPC).

In specific embodiments of the invention, the bulk material comprises or consists of a blend comprising the copolymer as described above and a second polymer component different from the copolymer and selected from poly(L-lactide), poly(D-lactide), poly[(L-lactide)-co-(ε-caprolactone)] and poly[(D-lactide)-co-(ε-caprolactone)], wherein the copolymer and the second polymer are selected such that the resulting polymer blend comprises a combination of constitution units derived from L-lactide and constitution units derived from D-lactide. In such polymeric blends stereocomplexes are formed not only to the surface layer but also within the bulk material. These stereocomplexes form crystallites functioning as net points physically (non-covalently) cross-linking the polymeric chains and imparting high elasticity and form stability to the material.

In embodiments, the second polymer component of the polymer blend is selected from PLLA and PDLA. In this case, its weight average molecular weight $M_w$ is preferably in the range of 1 to 40 kDa, preferably 2 to 20 kDa. By providing a molecular weight of the second polymer component of below 40 kDa, the mobility of the second polymer component within the blend is increased. As the corresponding PLLA- or PDLA-chains of the second polymer component serve as nucleation site for the formation of crystallites within the bulk material, the increased mobility leads to a higher velocity of the formation of crystallites and faster propagation of crystallization. On the other hand, by providing a molecular weight of the second polymer component of above 1 kDa, the size and hence the stability of the stereocomplexes within the bulk material are increased.

The second polymer component can be synthesised by homopolymerising the monomers L,L-dilactide or D,D-dilactide, respectively through ring opening polymerisation. In case the second polymer component is selected from poly[(L-lactide)-co-(ε-caprolactone)] or poly[(D-lactide)-co-(ε-caprolactone)], its synthesis can be done in the same way as described for the first component of the polymer blend.

Regarding the further properties of the P(LLA-co-CL) or P(DLA-co-CL) when used as the second polymer component the same consideration as set with respect of the first component apply.

In embodiments, the polymer blend comprises or consists of 80 to 99 wt % of the first copolymer and 1 to 20 wt % of the second polymer component. More preferably the polymer blend comprises or consists of 85 to 97 wt % of the first copolymer and 3 to 15 wt % of the second polymer component. Even more preferably, the polymer blend comprises or consists of 90 to 95 wt % of the first copolymer and 5 to 10 wt % of the second polymer component. By adjusting the mixing ratio of the both components the mechanical properties of the bulk material can be adjusted according to a desired appliance. Moreover, when the content of the second polymer component in the blend is more than 20 wt % the material becomes brittle if the second polymer component is of low molecular weight. Furthermore, below 1 wt % and above 20 wt % the elongation at break decreases. Accordingly, a weight content of the second polymer component in the range of 1 to 20 wt %, particularly of about 10 wt %, imparts the highest values of elastic modulus.

Preferred polymer blends according to the present invention are selected from: a blend comprising poly[(L-lactide)-co-(ε-caprolactone)] and poly(D-lactide) [P(LLA-co-CL)/PDLA], a blend comprising poly[(D-lactide)-co-(ε-caprolactone)] and poly(L-lactide) [P(DLA-co-CL)/PLLA], and a blend comprising poly[(L-lactide)-co-(ε-caprolactone)] and poly[(D-lactide)-co-(ε-caprolactone)] [P(LLA-co-CL)/P(DLA-co-CL)].

The polymer blend can easily be prepared by mixing the copolymer and the second polymer component in the target mixing ratio as set forth above. For this purpose, the single components may be added to a suitable solvent in the desired weight ratio and mixed to obtain a solution of the mixed polymer compounds. The solvent may then be removed. Alternatively, the single components may be dissolved individually in a suitable solvent followed by mixing the solutions and then removing the solvent. If desired, before removing the solvent, the mixed solution can be processed to a moulded object. In the mixed solution in a suitable solvent, for example but not limited to 1,1,1,3,3,3-Hexafluoroisopropanol or chloroform, no stereocomplexes are formed allowing an easy processing of the solution containing the polymer blend. Only after removing the solvent the stereocomplexes will be formed imparting a high elasticity and stability to the material due to formation of crystalline domains in the polymer blend.

The polymer blend of the bulk material is at room temperature highly elastic or even hyperelastic. Moreover, the material shows a high degree of shape stability. The term shape stability indicates the degree of restauration of the initial shape after releasing the deformation force. The blend preferably has an elongation at break in the range of 400 to 1000% at 25° C. The elongation at break can be determined by by uniaxial tensile testing of thin films and/or electrospun mats. Further, the polymer blend according to the present invention may have an elastic modulus in the range of 25 to 150 MPa at 25° C. (bulk polymer). The elastic modulus can be determined by uniaxial tensile testing of thin films and/or electrospun mats.

The polymer blend may be processed to a three-dimensional object by any standard moulding techniques. For instance, due to the fact that the stereocomplexes PLLA/PDLA within the blend are cleaved when the blend is dissolved, the material may easily be processed by dissolving the polymer blend in a suitable solvent, bringing the solution into the desired shape, and then removing the solvent. After removal of the solvent, the stereocomplexes will readily form even at room temperature or after annealing at elevated temperatures above the $T_g$ of PLA (50° C.) resulting in a highly elastic object having the desired three dimensional shape.

Surface-Functionalised Polymeric Object

The surface-functionalised polymeric object according to the invention may have any shape and may have a porous or compact (non-porous) structure.

As illustrated in FIG. 1, the surface-functionalised polymeric object 10 according to the invention comprises the bulk material 11 and the surface layer 12 comprising the functionalising species disposed on a surface of the bulk material 11.

Figure 1A:
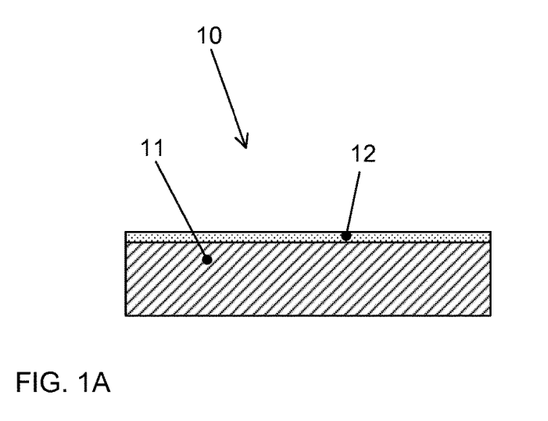
FIG. 1 a cross-section of surface-functionalised polymeric objects according to embodiments of the invention: A: surface-functionalised film, B: surface-functionalised fiber.

For instance, the object 10 may be a film of the bulk material 11, where one side of the film is covered with the surface layer 12 as shown in FIG. 1A. Alternatively, the surface layer 12 may be provided on both sides of the film (not shown).

Figure 1B:
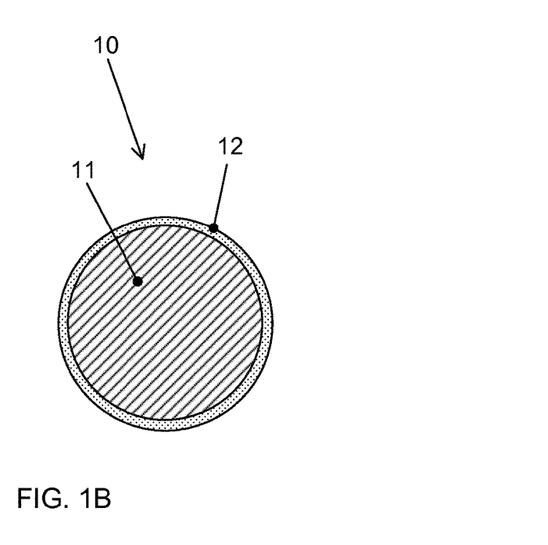

In preferred embodiments, the bulk material 11 has the form of fibers coated with the surface layer 12 as shown in FIG. 1B. The fibers have an average fiber diameter in the range of 0.5 to 10 μm, particularly in the range of 1 to 5 μm, preferably in the range of 1.3 to 3 μm. The fiber diameter can be controlled by varying the electrospinning process parameters.

On a more macroscopic scale, the surface-functionalised polymeric object according to the invention may have a porous, non-woven structure formed by the surface-functionalised fibers shown in FIG. 1B. Typically an average pore diameter may be controlled to be in the range of several hundreds of nanometres to several hundreds of micrometres by varying the electrospinning process parameters mentioned above. In examples, the average pore diameter is in the range of 1 μm to 200 μm. Due to its porosity, the non-woven object has substantially the high elasticity (elongation at break) described with respect of the polymer blend, but has lower E-moduli, typically in the magnitude of a few MPa. In embodiments, the object has an elongation at break at 25° C. in the range of 250 to 850%, particularly in the range of 350 to 700%. In further embodiments, the object has an elastic modulus at 25° C. in the range of 0.3 to 5 MPa, particularly in the range of 0.5 to 1.5 MPa.

Method of Producing a Surface-Functionalised Polymeric Object

In embodiments, the surface-functionalised polymeric object can be produced in a two-step procedure, comprising moulding the bulk material to any desired shape (film, fiber, etc.) applying common moulding techniques such as casting or electrospinning; followed by surface functionalisation of the bulk material with a solution of the functionalising species covalently modified with poly(D-lactide) or poly(L-lactide). The surface functionalisation may be perfected by any technique, such as dripping, spraying, dip-coating and the like. Presence of the solvent will enable sufficient mobility of polymer chains to allow the formation of the defining stereocomplexes.

However, in advantageous embodiments the surface-functionalised polymeric object according to the invention is produced by coaxial electrospinning as to form surface-functionalised fibers as shown in FIG. 1A.

The method comprises the steps of:
providing a first solution of the copolymer (or its blend with a different polymer) derived from a first comonomer and a second comonomer, the first comonomer being selected from L-lactide and D-lactide and forms sequences of oligo(L-lactide) or oligo(D-lactide) in the copolymer;
providing a second solution of the functionalising species having at least one chain of poly(D-lactide) or of poly(L-lactide) covalently bound to it; and subjecting the first and second solutions to coaxial electrospinning to produce fibers having a core of the copolymer (or its blend with a different polymer) and a surface layer (sheath) of the functionalising species.

In the first step any solvent or solvent mixture can be used that is capable of dissolving the copolymer (or its blend). In an example, the solvent is hexafluoro isopropanol (HFIP). The solvent used for dissolving the functionalising species may be the same as used for the copolymer or a different solvent.

In the step of electrospinning fibers are formed of the copolymer or its blend. The electrospinning apparatus comprises separate reservoirs for storing the first and second solutions (typically syringes). The both reservoirs are fluidly connected to a coaxial needle, such that the first solution is connected with the inner tube and the second solutions is connected with the circular outer tube. A collector is positioned with a predetermined distance to the needle tip and acting as target. A voltage is applied between the needle and the collector. During coaxial electrospinning the polymer solutions are pressed through a needle, charged by the voltage and accelerated in the electric field towards the collector.

The surface-functionalised polymer fibers may be deposited on the collector. The shape of the collector determines the shape of the object formed in the process. For example, the collector may be a simple flat plate. In this case, flat non-woven fiber structures are formed. However, for producing more complex shapes, the collector may have a shape which acts as mould for the shape of the object to be formed. Moreover, the collector may be a static one such that no movement relative to the needle tip occurs. In embodiments, the collector may be movable in one, two or three directions with respect to the needle tip and/or rotatable allowing the formation of complex three-dimensional structures by moving the collector.

There are various process parameters during coaxial electrospinning which can be varied in order to control the properties of the fibers. The process parameters comprise humidity of the atmosphere, the voltage applied to the needle and collector, the distance between needle and collector, polymer concentration of the polymer solution, solvent of the polymer solution, flow rate of the polymer solution through the needle, shape of the needle tip, rotation speed of the collector, etc.

In preferred embodiments, the process parameters during electrospinning are selected such that fast evaporation of the solvent is achieved. In other embodiments, the process parameters during electrospinning are selected as to control formation of the stereocomplexes. In still other embodiments, the process parameters during electrospinning are selected as to minimize shrinking of the spun fibers and structures formed thereof due to entropic relaxation.

After depositing the fibers, the object thus formed may be subjected to a thermal treatment, preferably at temperatures in the range of 60 to 120° C. The thermal treatment supports the formation of stereocomplexes and increases the crystallinity.

WORKING EXAMPLES

The invention is further explained by way of a specific working example. Here a lactide-based copolymer blend was functionalised with gelatin as functionalising species. Gelatin-functionalised fibers were produced by coaxial electrospinning and further analysed for their cytotoxicity.

Preparation of PDLA-Functionalised Gelatin

Figure 2:
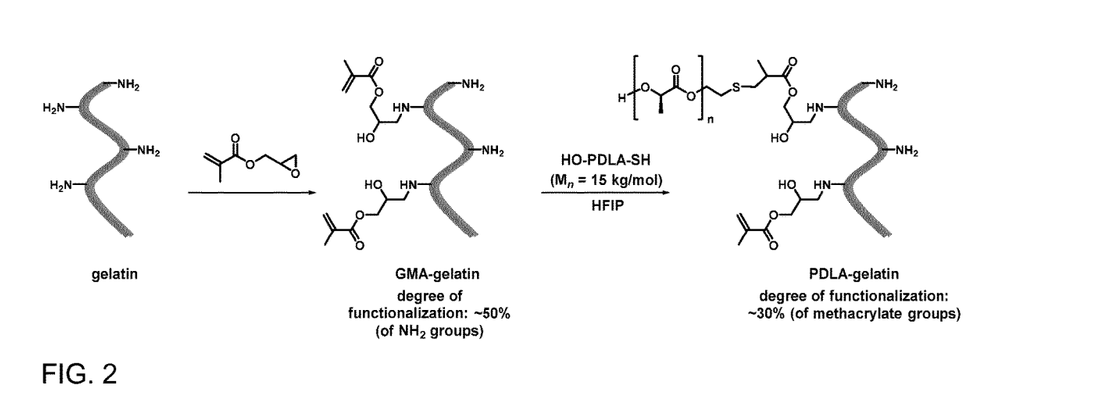
FIG. 2 PDLA-functionalisation of gelatin.

Gelatin was functionalised by reaction with glycidylmethacrylate (GMA), followed by covalent coupling of low molecular weight PDLA-thiol ($M_n$=15 kg·mol$^{-1}$) as outlined in FIG. 2. PDLA-thiol was synthesized by ring-opening polymerisation of D,D-lactide using bis(2-hydroxyethyl) disulfide as initiator, followed by reduction of the resulting PDLA-bisulfide with tri(n-butyl)phosphine to the PDLA-thiol.

A typical protocol for the synthesis of glycidylmethacrylate-functionalised gelatin (GMA-gelatin) is as follows:

A 10 wt % solution of gelatin (type A, from porcine skin, low endotoxin content, ~290 bloom, ~312 μmol $NH_2$ per g (TNBS-assay), 30.1 g) in pH 9.6 carbonate/bicarbonate buffer (50 mM) was magnetically stirred in a 1000 mL round bottom flask at 50° C. until complete dissolution (ca. 1 h). Glycidylmethacrylate (GMA) (31.5 mL, 32.8 g, 0.23 mmol) was added dropwise and the resulting mixture was stirred at 50° C. for 3 h. The product was precipitated in a 7-fold volume excess ethanol during gentle stirring, and soaked overnight, filtered and washed with ethanol. The precipitated gelatin was cut into smaller pieces and dried at 40° C. under reduced pressure. The yield of GMA-gelatin was typically in the range of 27-28 g. TNBS-assay of GMA-Gelatin usually conferred to 160-175 μmol methacrylate groups per g (50-55% degree of functionalisation=45-50% of residual $NH_2$ groups).

A typical protocol for the synthesis of PDLA-functionalised gelatin (PDLA-gelatin) is as follows: A 500 mL round bottom flask was loaded with GMA-gelatin (cut into small lumps of 0.5 cm size; 5.00 g; about 0.84 mmol methacrylate groups). HFIP (210 mL) was added and the mixture was vigorously stirred at 48° C. for 3 days until the gelatin lumps were dissolved and a turbid, homogenous slurry was obtained. A solution of freshly prepared PDLA-thiol (10.0 g, about 0.63 mmol of thiol groups) in HFIP (50 mL) was added to the mixture and vigorous stirring at 48° C. was continued for 22 h. The reaction mixture was then slowly poured into vigorously stirred $CHCl_3$ (2000 mL). After decantation of the supernatant, water (200-250 mL) was added to the precipitated slurry and the resulting mixture was vigorously stirred at 48° C. (>400 rpm) for several hours while residual organic solvents were allowed to evaporate and stirring was continued at 48° C. overnight to provide a milky solution. Excess PDLA (that was not covalently bound to gelatin) was precipitated by centrifugation, the product was obtained after lyophilization of the supernatant followed by drying under reduced pressure. The yield of PDLA-gelatin was typically about 5 g. The degree of functionalisation was determined by $^1$H-NMR spectroscopy, typically about 30% of the methacrylate groups were reacted with PDLA-thiol.

A typical protocol for the synthesis of PDLA-disulfide is as follows:

A 500 mL Schlenk-flask was loaded with D,D-dilactide (100.0 g, 639.8 mmol) under argon atmosphere and placed into a preheated oil bath at 133° C. The dilactide was magnetically stirred until a colorless melt was obtained. Bis(2-hydroxyethyl)disulfide (505 mg, 3.27 mmol) was added via syringe and stirring at 133° C. of the mixture was continued for 5 min., then a dilute solution of Sn(oct)$_2$ in anhydrous THF (112 mg, 0.278 mmol, e.g. about 5.05 mL of a THF solution with c=22.3 mg/mL) was added dropwise and the resulting mixture was stirred for 1 h at 133° C., during that time the melt became highly viscous and solidified. The crude product was allowed to cool to room temperature, dissolved in 400 mL chloroform (24 h at 50°

C.), and precipitated into a 10-fold excess of methanol. The obtained precipitate was then dried at 60° C. under reduced pressure. The yield of PDLA-bisulfide typically was about 95 g and the number average molecular weight ($M_n$) was analysed to be around 30 kg·mol$^{-1}$ as determined by $^1$H-NMR (25 kg·mol$^{-1}$ as determined by universally calibrated GPC).

A typical protocol for the synthesis of PDLA-thiol is as follows:

A 500 mL Schlenk-flask was loaded with PDLA-disulfide (25.0 g, 0.82 mmol) and chloroform (400 mL) under argon atmosphere. The reaction mixture was magnetically stirred for about 1 h until a clear solution was obtained. 5.0 mL of tri(n-butyl)phosphine were added via syringe and stirring for 1 h at room temperature was continued. The solution containing the crude product was then precipitated into a 10-fold excess of cold n-hexane. The obtained precipitate was dried at 60° C. under reduced pressure. The yield of PDLA-thiol typically was about 24-25 g and the number average molecular weight ($M_n$) was analysed to be around 15 kg·mol$^{-1}$ as determined by $^1$H-NMR (17 kg·mol$^{-1}$ as determined by universally calibrated GPC).

Preparation of the Copolymer Blend Components P(LLA-Co-CL) 67/33 and PDLA-16k] and Characterisation of the Corresponding Blend 95:5 w/w The synthesis of the copolymer [P(LLA-co-CL) 67/33] was performed by tin(II) 2-ethylhexanoate (Sn(oct)$_2$) catalysed ring-opening polymerisation of a mixture of ε-caprolactone and L,L-dilactide in the melt as follows: A 500 mL flame-dried three-neck-flask (equipped with magnetic stirring rod, rubber septum, PTFE valve and glass stopper) under argon atmosphere was loaded with L,L-dilactide (60.0 g, 416 mmol) and ε-caprolactone (40.0 g, 350 mmol), that was purified by distillation. The reaction vessel was placed into a preheated oil bath (140° C.) and the mixture was magnetically stirred until complete melting/dissolution. Then a dilute solution of Sn(oct)$_2$ in anhydrous THF (5.6 mL with a concentration of 22.28 mg/mL Sn(oct)$_2$) was added dropwise and the resulting mixture was stirred for 53 h at 140° C. to become a highly viscous polymer melt. A fraction of the crude product of about 10 g was removed from the middle of the reaction vessel for analysis. The reaction vessel was then removed from the oil bath and the remaining crude product was allowed to cool to room temperature, dissolved in chloroform (c=50 g/L), followed by precipitation in a 10-fold excess of methanol. The precipitate was dried under reduced pressure at 60° C. The yield of the purified copolymer was 69 g. The molar comonomer ratio in the copolymer of LLA:CL=67/33 was determined by $^1$H-NMR-spectroscopy by comparison of the peak integrals of CH-moieties related to lactide (5.06-5.20 ppm) and of CH$_2$-moieties related to ε-caprolactone (4.02-4.15 ppm). Due to the removal of a fraction from the crude product prior to purification, the LA/CL ratio of the purified copolymer differed from the molar ratio of employed monomers (LA/CL=70/30) in the synthesis, as the crude polymerisation product displayed a heterogeneous distribution of LA and CL units, with more LA-rich copolymer in the middle of the reaction vessel, and more CL-rich copolymer next to the walls of the reaction vessel, respectively. The purified product (after dissolution and precipitation) displayed a homogenous distribution of LA and CL units. The dyad ratio (DR) of LA-LA/LA-CL=3.0:1 was determined by integrating the signals related to LA-LA dyads (5.13-5.20 ppm) and those related to LA-CL dyads (5.07-5.13 ppm) in the $^1$H-NMR spectrum and by comparing the integrated intensities.

A glass transition temperature ($T_g$) of −10° C. for the purified copolymer was determined by differential scanning calorimetry (DSC, $2^{nd}$ heating cycle). A weight average molecular weight ($M_w$) of 145±7 kg·mol$^{-1}$ of the copolymer was determined by universally calibrated gel permeation chromatography (GPC).

The synthesis of PDLA-16K was performed by tin(II) 2-ethylhexanoate (Sn(oct)$_2$) catalysed ring-opening polymerisation of D,D-dilactide in the melt as follows: A 500 mL flame-dried Schlenk-flask (equipped with magnetic stirring rod, NS 29 rubber septum and PTFE valve) under argon atmosphere was loaded with D,D-dilactide (20 g, 138.7 mmol). The reaction vessel was placed into a preheated oil bath (135° C.) and the mixture was magnetically stirred until complete melting. Anhydrous 1-hexanol (188 mg, 1.84 mmol) was added dropwise via syringe to the stirred melt of the dilactide. After 5 minutes a dilute solution of Sn(oct)$_2$ in anhydrous THF (1.0 mL with a concentration of 22.28 mg/mL Sn(oct)$_2$) was added dropwise and the resulting mixture was stirred for 1 h at 135° C. to become a highly viscous polymer melt that solidified towards the end of the reaction. The reaction vessel was removed from the oil bath and the crude product was allowed to cool to room temperature, dissolved in chloroform (250 g/L), followed by precipitation in a 10-fold excess of cold methanol. The precipitate was dried under reduced pressure at 60° C. The yield of purified PDLA-16K was 18 g, with a weight average molecular weight as determined by GPC (universal calibration) of 16±2 kg·mol$^{-1}$.

To characterize the physical properties of the bulk polymer blend [P(LLA-co-CL) 67/33+PDLA-16K 95:5 w/w] a solution-casted film was prepared as follows: a mixture of 570 mg P(LLA-co-CL) 67/33 and 30 mg PDLA-16K was added to 12 mL of chloroform. The mixture was agitated at 58° C. and 700 rpm for 2 h using a thermomixer. The resulting solution was cooled to room temperature and poured into a PTFE evaporation dish. The dish was tightly covered with aluminum foil and left for evaporation of the solvent in the hood for several days, followed by drying under reduced pressure at 60° C. overnight. The obtained polymer blend film had a thickness of 95±7 μm.

The film was characterised by uniaxial tensile testing to determine the mechanical properties of the bulk polymer blend. The material displayed an elastic modulus of E=26±2 MPa, a tensile strength of $\sigma_{max}$=24±5 and an elongation at break of $\varepsilon_b$=889±83%. A total crystallinity of the polymer blend film of 24.9±0.3% was determined by wide angle x-ray scattering (WAXS) and specific signals for crystallites originating from stereocomplexes of the oligo-LLA segments of [P(LLA-co-CL) 67/33 and PDLA-16K were detected at 2θ=12° and 21° (in addition to signals corresponding to oligo-LLA homocrystallites at 2θ=17° and 19°).

Preparation of Surface-Functionalised Polymeric Fiber Mats (Patches) by Coaxial Electrospinning A first solution of the polymer blend of 8% weight-per-volume (w/v) [95:5 w/w of P(LLA-co-CL) 67/33 and PDLA-16k] in hexafluoro isopropanol was prepared by magnetic stirring at room temperature. A second solution of 1% w/v of the PDLA-gelatin in hexafluoro isopropanol was prepared accordingly. Both solutions were simultaneously subjected to coaxial electrospinning. The spinning parameters are summarized in Table 1.

TABLE 1

Parameters for coaxial electrospinning of [95:5 w/w P(LLA-co-CL) 67/33 + PDLA-16k] and of PDLA-gelatin.

| solution | C | V | D | $\dot{V}$ | H | mandrel diameter (rotation speed) |
|---|---|---|---|---|---|---|
| Core: [95:5 w/w P(LLA-co-CL) 67/33 + PDLA-16k] in HFIP | 8% w/v | 15-21 kV | 30 cm | 2.12 mL/h | <10% | 20 cm (10 rpm) |
| Shell: PDLA-gelatin in HFIP | 1% w/v | | | | | |

Figure 3:
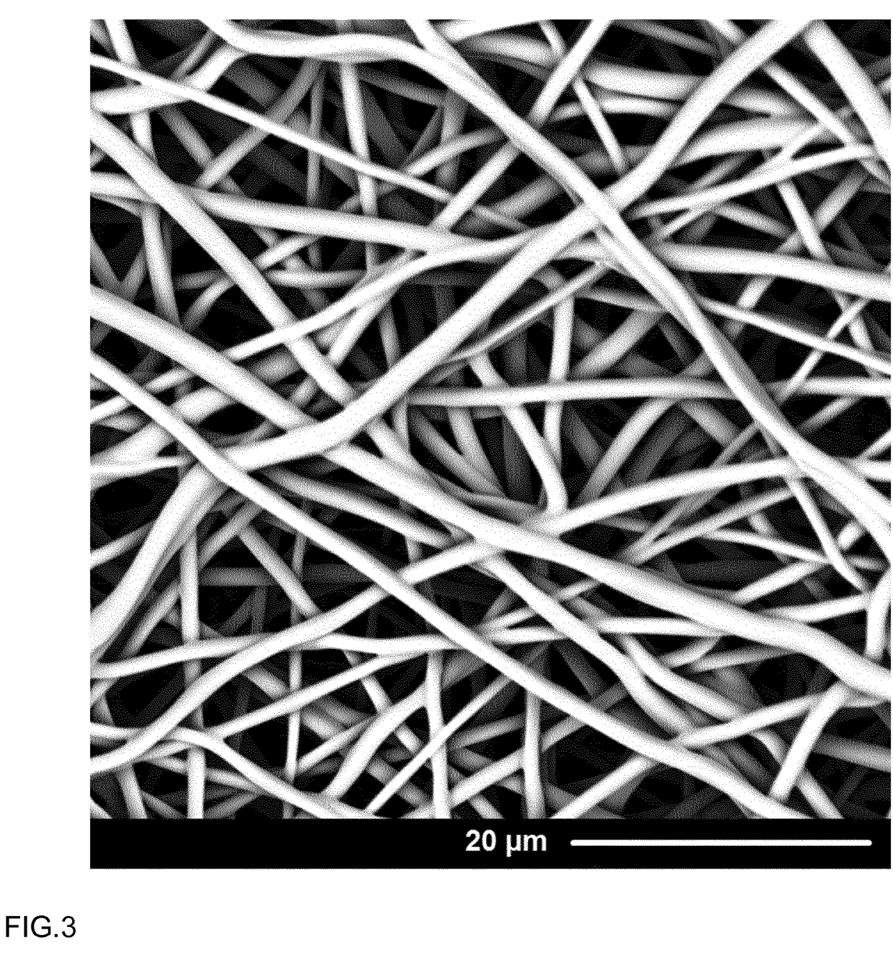
FIG. 3 Scanning electron microscopy (SEM) image of a coaxially electrospun patch comprising polymer blend fibers of [95:5 w/w [P(LLA-co-CL) 67/33]+PDLA-16k] as inner core and an outer thin layer of PDLA-functionalised gelatin.

HFIP: hexafluoro isopropanol;
C: concentration;
V: voltage;
D: distance between needle and collector;
$\dot{V}$: flow rate;
H: relative humidity The resulting product was a porous non-woven patch of electrospun fibers displaying an average fiber diameter of 1.4±0.3 μm as determined from scanning electron microscopy (SEM) images (FIG. 3). The fibers having an inner core of the lactide-based polymer blend [95:5 w/w of P(LLA-co-CL) 67/33 and PDLA-16k] and an outer thin layer of the functionalising species (PDLA-gelatin) according to the structure illustrated in FIG. 1B.

Figure 4:
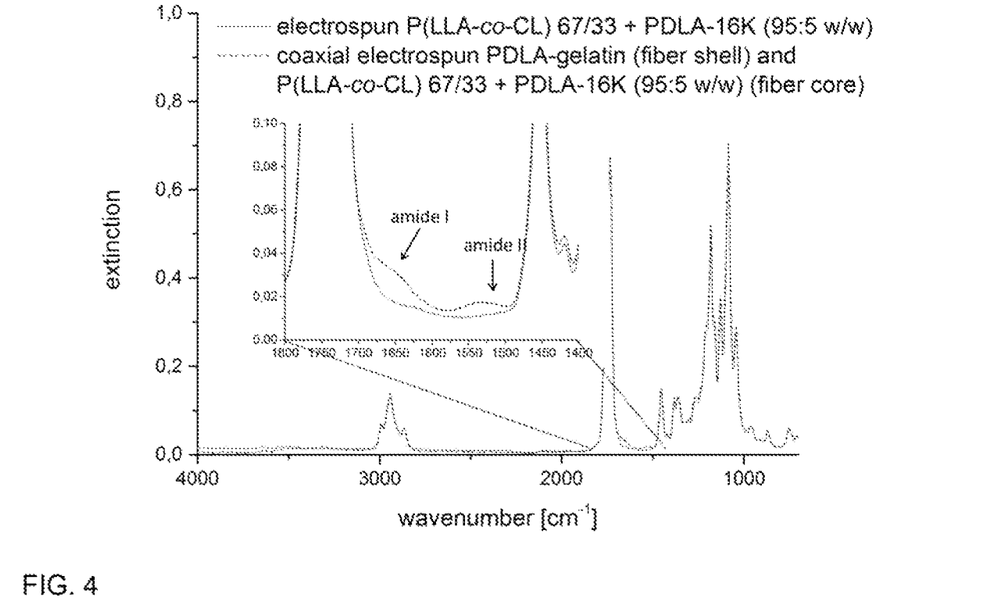
FIG. 4 ATR-FTIR spectra of an electrospun blend [95:5 w/w [P(LLA-co-CL) 67/33]+PDLA-16k]; and of a coaxial electrospun blend [95:5 w/w [P(LLA-co-CL) 67/33]+PDLA-16k] with PDLA-functionalised gelatin.

The patches were analyzed by attenuated total reflection Fourier-transform infrared spectroscopy (ATR-FTIR). The ATR-FTIR spectrum of the coaxial electrospun functionalised material is depicted in FIG. 4 in comparison with the non-functionalised electrospun pure polymer blend [95:5 w/w P(LLA-co-CL) 67/33+PDLA-16K]. The additional small bands at about 1645 cm$^{-1}$ and 1540 cm$^{-1}$ correspond to the amide I and II carbonyl vibrations of proteins (gelatin) and thus prove the presence of gelatin on the surface of the polymer fibers.

Figure 5:
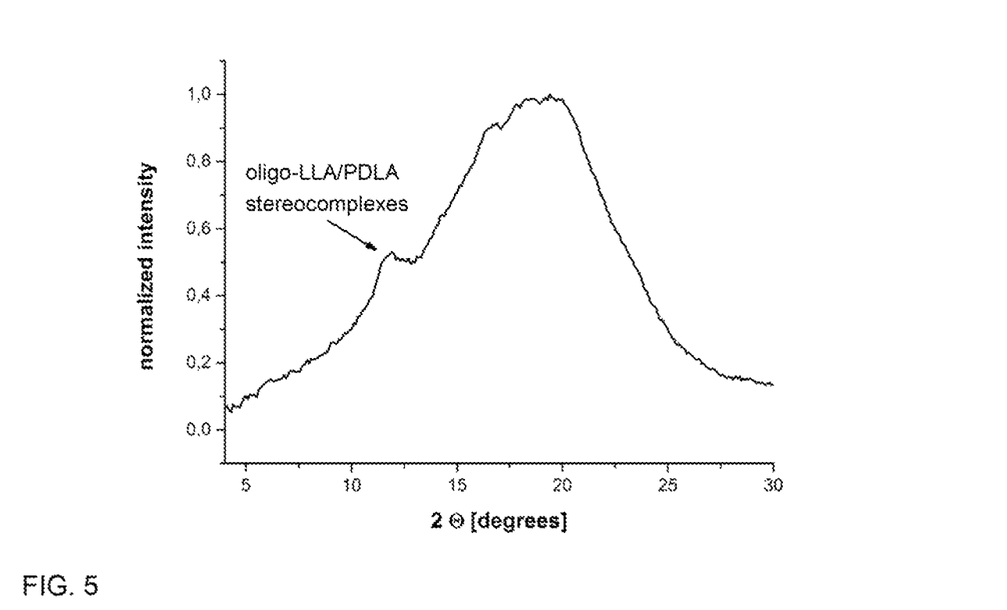
FIG. 5 WAXS diffraction pattern of a coaxial electrospun blend [95:5 w/w [P(LLA-co-CL) 67/33]+PDLA-16k] with PDLA-functionalised gelatin.

The wide angle x-ray scattering (WAXS) pattern of a such a coaxial electrospun patch is shown in FIG. 5. The Signal at 2θ=12° (marked with arrow) confirms the presence of oligo-LLA/PDLA stereocomplexes.

Cytotoxicity Tests

A coaxial electrospun patch produced as described above passed the cytotoxicity testing according to DIN EN ISO 10993-5 and 10993-12 (indirect testing). A patch sample was incubated in cell culture medium for 72 h at 37° C. and the extract was used for culturing L929 Cells (mouse fibroblasts). Polystyrene was used in the negative and positive control tests.

Figure 6:
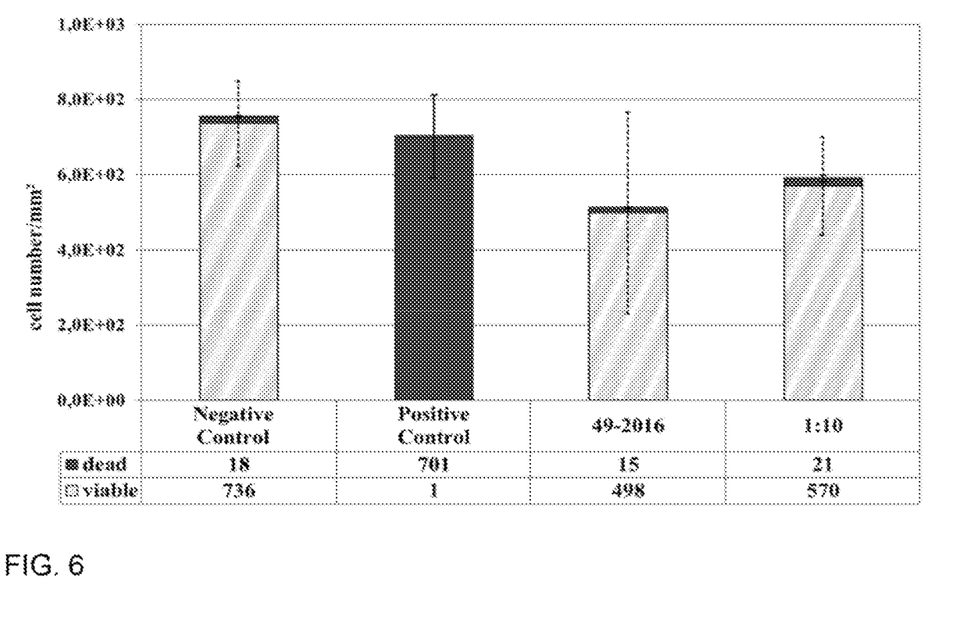
FIG. 6 Viability of L929 cells 48 h after cell growth with cell culture medium on polystyrene (negative control, positive control), with an extract of the sample (incubation of sample in cell culture medium for 72 h at 37° C.) and diluted sample extract; fluorescein-diacetate (FDA) and propidium-iodide staining; means±standard deviation.
Figure 7:
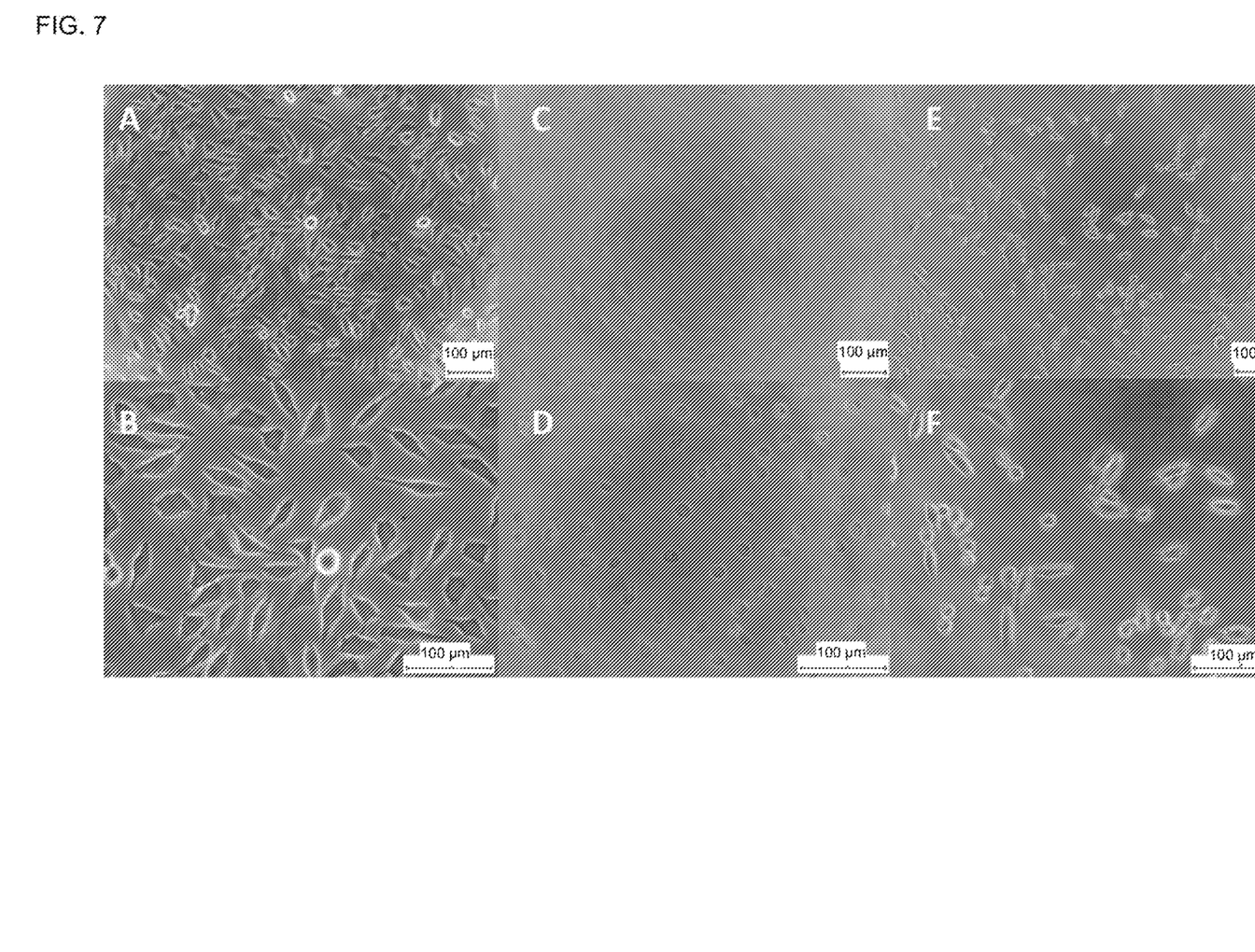
FIG. 7 L929 cells 48 h after culturing with pure culture medium (A, B, negative control) and a 72 h-extract of the sample (E, F; undiluted); positive controls (C, D). Phase contrast microscopy in transmission, primary magnification 10× (A, C, E) and 20× (B, D, F); scale bar representing 100 μm.
Figure 8:
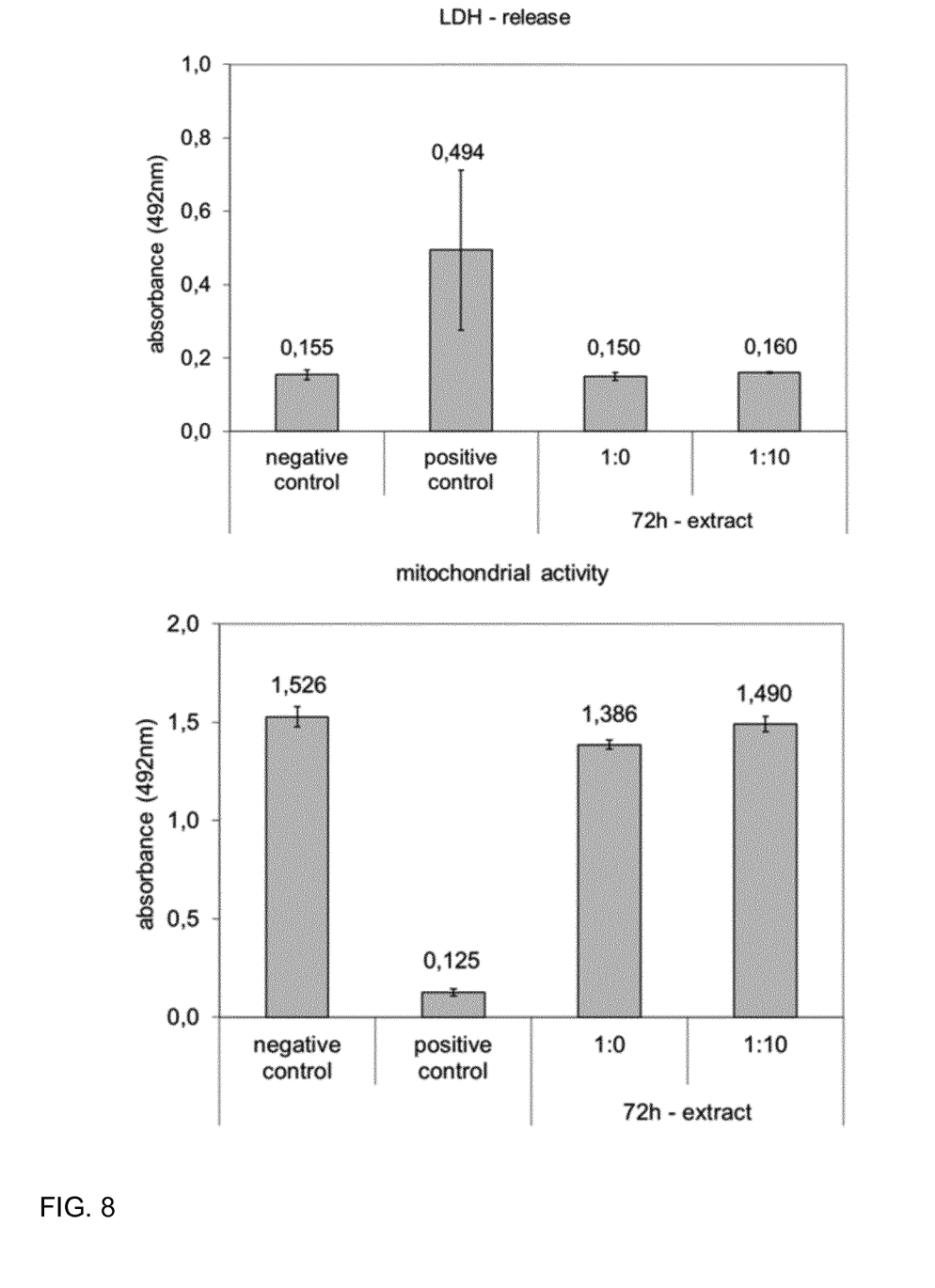
FIG. 8 Lactate dehydrogenase (LDH) activity in the extracellular fluid and the mitochondrial activity of the cells 48 h after culturing L929 cells with pure culture medium (negative control), with a 72 h-extract of the sample; and positive control (medium with 1 mM $CuCl_2$ resp. Cell Lysis Solution); means±standard deviation, n=4.

As illustrated in FIG. 6 the cells maintained a high viability. Further as observed in transmission phase contrast microscopy the cells showed little morphological changes (FIG. 7). No significant lactate dehydrogenase (LDH)-release (FIG. 8, above) and high mitochondrial activity (FIG. 8, below) were measured.

In summary the data confirmed the suitability of the coaxial electrospun patches for medical applications.

The invention claimed is:

1. A surface-functionalised polymeric object (10), comprising:
    a bulk material (11) comprising a copolymer containing constitution units derived from a first comonomer and constitution units derived from a second comonomer, the first comonomer being L-lactide or D-lactide and forming sequences of oligo(L-lactide) or oligo(D-lactide) in the copolymer, the copolymer having a substantially random, partially blocky structure with a dyad ratio of (lactide-lactide)-dyads to (lactide-second comonomer)-dyads of at least 2.0:1; and
    a surface layer (12) disposed on a surface of the bulk material (11), the surface layer (12) comprising a functionalising species and at least one chain of poly(D-lactide) or of poly(L-lactide) covalently bound to the functionalising species, the at least one chain being poly(D-lactide) when oligo(L-lactide) segments are present in the copolymer and being poly(L-lactide) when oligo(D-lactide) segments are resent in the copolymer wherein the surface layer (12) is attached to the bulk material (11) via stereocomplexes formed between the poly(D-lactide) chain(s) of the functionalising species and the oligo(L-lactide) sequences contained in the copolymer or via stereocomplexes formed between the poly(L-lactide) chain(s) of the functionalising species and the oligo(D-lactide) sequences contained in the copolymer, respectively.

2. The surface-functionalised polymeric object according to claim 1, wherein the functionalising species of the surface layer (12) is a macro-molecule, comprising synthetic polymers and biopolymers; such as proteins, polysaccharides, glycoproteins, proteoglycans, nucleic acids; or a low-molecular weight molecule, comprising synthetic molecules or biomolecules.

3. The surface-functionalised polymeric object according to claim 1, wherein the functionalising species has 2 or more chains of poly(D-lactide) or of poly(L-lactide) covalently bound to it.

4. The surface-functionalised polymeric object according to claim 1, wherein the copolymer of the bulk material (11) has a dyad ratio of (lactide-lactide)-dyads to (lactide-second comonomer)-dyads of at least 2.5:1.

5. The surface-functionalised polymeric object according to claim 1, wherein a weight content of L-lactide or D-lactide in the copolymer is in the range 55 to 90 wt %, based on the total weight of the copolymer.

6. The surface-functionalised polymeric object according to claim 1, wherein the copolymer of the bulk material (11) is selected from poly[(L-lactide)-co-(e-caprolactone)] and poly[(D-lactide)-co-(e-caprolactone)].

7. The surface-functionalised polymeric object according to claim 1, wherein the copolymer has a weight average molecular weight M$_w$ of at least 80 kDa.

8. The surface-functionalised polymeric object according to claim 1, wherein the bulk material (11) comprises a blend comprising the copolymer and a second polymer component different from the copolymer and selected from poly(L-lactide), poly(D-lactide), poly[(L-lactide)-co-(e-caprolactone)] and poly[(D-lactide)-co-(e-caprolactone)], wherein the copolymer and the second polymer are selected such that the resulting polymer blend comprises a combination of constitution units derived from L-lactide and constitution units derived from D-lactide.

9. The surface-functionalised polymeric object according to claim 8, wherein the blend comprises or consists of 80 to 99 wt % of the copolymer and 1 to 20 wt % of the second polymer.

10. The surface-functionalised polymeric object according to claim 8, wherein the second polymer has a weight average molecular weight $M_w$ in the range of 2 to 20 kDa.

11. The surface-functionalised polymeric object according to claim 8, wherein the polymer blend has an elongation at break in the range of 400 to 1000% at 25° C. and/or has an elastic modulus in the range of 25 to 150 MPa at 25° C.

12. The surface-functionalised polymeric object according to claim 1, wherein the bulk material (11) has the form of fibers coated with the surface layer (12).

13. The surface-functionalised polymeric object according to claim 12, wherein the fibers have an average fiber diameter in the range of 0.5 to 10 µm.

14. The method of producing a surface-functionalised polymeric object according to claim 1, comprising:
providing a first solution of the copolymer derived from a first comonomer and a second comonomer, the first comonomer being selected from L-lactide and D-lactide and forming sequences of oligo(L-lactide) or oligo(D-lactide) in the copolymer;
providing a second solution of the functionalising species having at least one chain of poly(D-lactide) or of poly(L-lactide) covalently bound to it; and
subjecting the first and second solution to coaxial electrospinning to produce fibers having a core (11) of the copolymer and a surface layer (12) of the functionalising species.

* * * * *